(12) United States Patent
Doering

(10) Patent No.: US 7,223,610 B2
(45) Date of Patent: May 29, 2007

(54) DIRECT PHOSPHORYLATION STATE MONITORING ON BIOMOLECULES

(75) Inventor: Klaus Doering, Salzburg (AT)

(73) Assignee: Tecan Trading AG, Mannedorf (CH)

( * ) Notice: Subject to any disclaimer, the term of this patent is extended or adjusted under 35 U.S.C. 154(b) by 410 days.

(21) Appl. No.: 10/820,404

(22) Filed: Apr. 8, 2004

(65) Prior Publication Data

US 2004/0259183 A1    Dec. 23, 2004

(30) Foreign Application Priority Data

Apr. 10, 2003 (CH) .................................... 0653/03

(51) Int. Cl.
*G01N 33/53* (2006.01)
(52) U.S. Cl. ........................ 436/800; 435/17
(58) Field of Classification Search ..................... None
See application file for complete search history.

(56) References Cited

U.S. PATENT DOCUMENTS 6,410,255 B1    6/2002    Pollok et al.

FOREIGN PATENT DOCUMENTS

WO    WO 00/42214    7/2000
WO    WO 00/72016    11/2000

OTHER PUBLICATIONS

Fowler et al. Analytical Biochemistry 2002;308:223-231.*

* cited by examiner

*Primary Examiner*—Ralph Gitomer
*Assistant Examiner*—Bin Shen
(74) *Attorney, Agent, or Firm*—Notaro & Michalos P.C.

(57) ABSTRACT

Method for measuring the presence or absence of chemical groups, in particular phosphate groups, attached to biological molecules in a sample in which these molecules are tagged with fluorescent markers and these fluorescent markers are activated by means of irradiating the sample with light. The method is characterized by the following steps: a) Use of a fluorescent marker, the fluorescence lifetime of which assumes a different value depending upon the presence or absence of phosphate groups attached to the biomolecule; b) Measurement of the fluorescence lifetime of the fluorescent marker attached to a biomolecule and selected in accordance with Step a); c) Classification of the biomolecules in accordance with the presence or absence of phosphate groups attached to these, based on the different lifetime of each.

12 Claims, 1 Drawing Sheet

DIRECT PHOSPHORYLATION STATE MONITORING ON BIOMOLECULES

RELATED APPLICATIONS

Figure 1:
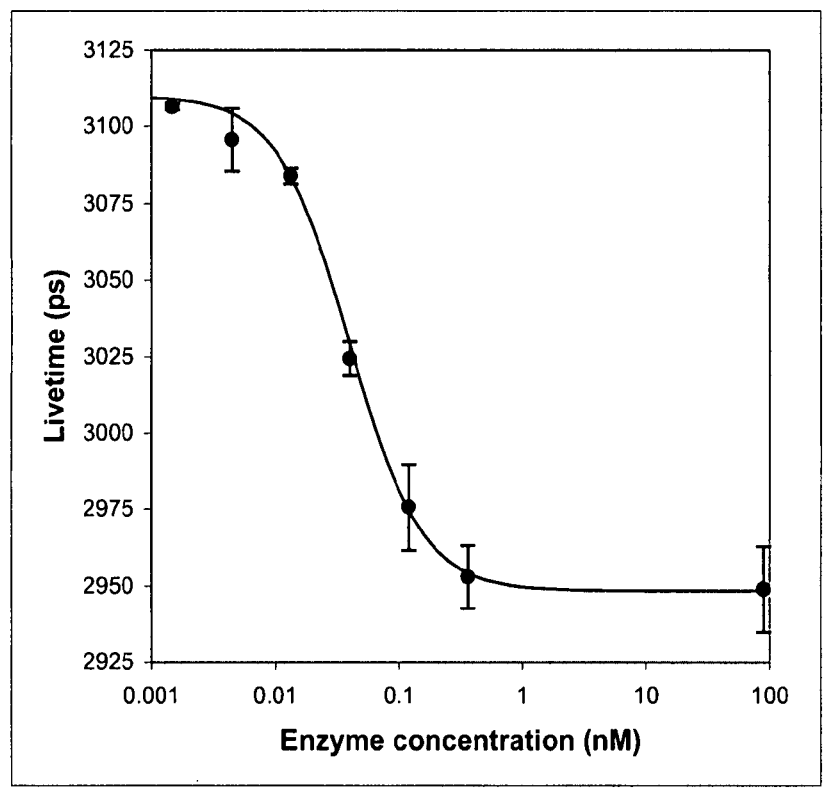

This application claims priority of the Swiss patent application No. CH 0653/03 filed on Apr. 10, 2003.

TECHNICAL FIELD OF THE INVENTION

The invention relates to a method for measuring chemical groups attached to biological molecules, in particular for measuring the presence or absence of phosphate groups attached to biological molecules.

The classes of enzymes which catalyze the attachment (phosphokinase) and/or the removal (phosphatase) of phosphate residues to and from biomolecules is of great biological and pharmacological importance. In order to measure the efficiency of enzyme functionality it is possible, among other means, to utilize the concentration of reactants or products of the reaction, that is for instance, the quantity of phosphorylated biomolecules in the sample volume.

Methods for measuring the presence and/or absence of chemical groups, for instance of phosphate groups, attached to biological molecules are known per se and include for instance, the use of fluorescence polarization. Such fluorescence polarization measurements are based on changes in the volume of the molecules subject to measurement. Many of the reactions involving biological processes based on an increase in volume, such as those involving receptor-ligand bonds, antibody-antigen bonds, DNA hybridization or DNA protein bonds, as well as those processes involving a reduction in volume, such as enzymatic degradation or dissociation reactions, can be measured directly by means of fluorescence polarization.

Such tests employ the following approach: An unphosphorylated biomolecule is incubated with an enzyme which binds a phosphate group to this molecule, namely with a phosphokinase, or a phosphorylated peptide is incubated with an enzyme that removes the phosphate group from this peptide, that is with a phosphatase. The change in the volume of a biological molecule by adding or removing a small chemical group, such as for instance a phosphate, sulfate or oxalate group, is not significant enough for it to be detected directly by means of fluorescence polarization. As a rule, in order to enhance the volume effect an auxiliary molecule is attached to the biological molecule being analyzed. These auxiliary molecules, in the form of antibodies, have to be selected in such a way that they only ever form a bond with the peptides being analyzed when these peptides truly include a phosphate group. This ensures that there is a significant difference in terms of their volume between the phosphopeptide/antibody complexes being measured by means of fluorescence polarization and the non-phosphorylated peptides without any attached auxiliary molecules. This commercially available approach was originally developed to provide a non-destructive marker which facilitated the tracking of enzyme functionality. In a situation in which the pharmacological efficacy of chemical substances is being tested (i.e. a drug discovery situation), such assay substances are added to the system, with the standardized fluorescence polarization measurement providing information as to whether the assay substance produces the desired modulation effect on the enzyme or not.

RELATED PRIOR ART

All known methods for ascertaining phosphorylation and/or dephosphorylation are based on the addition of auxiliary molecules, such as the method for instance disclosed in U.S. Pat. No. 6,410,255. In addition to antibodies, other chemical compounds can also be employed as the auxiliary molecules for detecting the phosphorylation of a biomolecule, thus being capable of differentiating one state of phosphorylation from another. If one were to attempt to measure the concentration of other reactants or products of a phosphorylation reaction using an alternative method, one would have to employ chemical methods involving more complex additions than is the case with fluorescence polarization.

OBJECTS AND SUMMARY OF THE INVENTION

In accordance with the object of the present invention, an alternative method is proposed for detecting a chemical reaction at a biological molecule in a simple manner, such as for instance phosphorylation or dephosphorylation of a peptide.

This object is achieved by means of the characteristics specified in the independent claim 1. Preferred embodiments of the method in accordance with the invention and/or additional inventive elements are derive from the dependent claims.

It has been known for a long time that the fluorescence polarization signal emitted by a sample tagged with a fluorescent marker is not altered significantly simply by adding or removing a phosphate group and that charges can alter the fluorescence lifetime of fluorescent dyes. However, the fact that it is sufficient to add a phosphate group to a biomolecule supplemented with a fluorescent marker in order to generate a workable signal, was a complete surprise.

Consequently, the present invention is based upon the unexpected and surprising discovery that by adding or removing a phosphate group to or from a biological molecule respectively, the fluorescent lifetime of fluorophores attached to these samples, reflecting the presence or absence of a phosphate group, is altered significantly.

DETAILED DESCRIPTION OF THE INVENTION

The mechanism upon which the present invention is based is not fully understood. However, it is assumed that it involves an interaction between the fluorescent marker and a charged residue, which is attached in the vicinity of the binding site of the fluorescent marker on the same biomolecule and/or is located within the spatial range of the fluorescent marker. Fluorescein was found to be a fluorescent marker, the fluorescence lifetime of which changes significantly in response to the presence or absence of a phosphate group. However, the invention encompasses not only the use of fluorescein; the general assumption is made that every chemical reaction involving a biomolecule, which produces one or more charged chemical residues, can be detected properly by measuring the fluorescence lifetime. The assumption is made that such or similar results can also be used for establishing the presence of other enzyme reactions, if in accordance with the present invention, the fluorescence lifetime of suitable fluorescent markers attached to the corresponding biomolecules is measured.

It is known that enzymes catalyze many different types of chemical reactions. The following table lists the most common reactions observed in living systems and the associated enzyme classes which play an important role in these reactions:

| Reaction | Impact | Enzyme class | Enzyme name |
|---|---|---|---|
| Oxidation; Reduction | C—O, C—C or C—N bonds | I | oxido-reductases |
| Intramolecular and intermolecular transfer | Transfer of functional groups | II | transferases |
| Hydrolysis | Ester, ether and amides | III | hydrolases |
| Elimination; Addition | C—O, C—C or C—N bonds | IV | lyases |
| Isomerization | Steric modifications | V | isomerases |
| Binding | Ester, thiolester and amide bonds | VI | ligases |

Using the method in accordance with the invention, enzyme reactions which enrich molecules by means of a catalytic process can be detected and quantified.

Enzyme Class I:

Oxidoreductases catalyze redox reactions, with oxidation resulting in the loss of electrons and a reduction in the acquisition of electrons. Consequently, it is possible for instance, that the modification of a fluorescence lifetime signal can be observed for a fluorescent marker which is located in the direct vicinity of an active oxidoreductase site, indicating the migration of electrons through the various amino acid side chains within the enzyme or substrate during the catalytic transition. This fluorescent chain has already been detected in Class I enzymes: the reduction of $NAD^+$ to NADH by means of dehydrogenases has shown that $NAD^+$ is not fluorescent, in contrast to NADH.

Enzyme Class II:

Transferases are enzymes which catalyze the transfer of a functional group from one substituent to another, which can occur within the same molecule or between different molecules. Typical examples for this class are kinases, which transform ATP to a protein or peptide. Similar effects involving the fluorescence lifetime, such as for the phosphokinase reactions described below, can be expected for thiolases and other transferases.

Enzyme Class III:

Hydrolases are enzymes which catalyze the hydrolysis of carboxylic acid esters, hemiacetal ethers (glycosyl compounds), thioethers, amides (peptide bonds) and acid anhydrides. This group also includes the phosphatases, as they cleave a phosphate group into water. The information for Class I and II also applies with respect to this class.

Enzyme Class IV:

Lyases are enzymes which catalyze the elimination or addition of chemical groups. One example is the elimination of a CO group, known as decarboxylation. Due to the fact that the decarboxylases generally give up a pair of electrons in order to catalyze the decarboxylation reaction, as a change to the "electronic signature" of the substrate can be anticipated during the course of the decarboxylation reaction, this class of reactions and/or enzymes should also be able to be analyzed using lifetime fluorometry.

Enzyme Class V:

Isomerases catalyze certain intramolecular rearrangements, such as racemization, epimerization, cis-trans-conversions and enol-keto-tautomerization. As massive electron movement is also expected during enol-keto-tautomerization, it should also be possible to measure a change in the fluorescence lifetime in this case.

Enzyme Class VI:

Ligases are enzymes which catalyze a bond between molecules, using the energy they gain from cleaving the ATP (or a similar nucleoside triphosphate). This class includes, for instance, fatty acid synthetases and DNA polymerases. Similarly, an assumption can be made with respect to these enzymes that it is highly likely that a catalytic reaction produced by these enzymes will result in a significant change to the fluorescence lifetime of a fluorophore located in the vicinity of an enzyme's active site.

In accordance with the present invention a single fluorescent marker suffices if it is located in the vicinity and/or in the sphere of influence of a chemically active group on the biomolecule. One condition with respect to the fluorescent marker is that it reacts to an alteration in the charge density and/or the configuration in its direct molecular environment by altering its fluorescence lifetime. The signal generated in this manner is thus much more direct than the method representing the state of the art, which employs the addition and binding of auxiliary molecules.

The list of biological molecules (of natural and synthetic origin) provided here in relation to the present invention is by no means exhaustive and is purely for exemplary purposes:

- molecules generated by biological or synthetic means encompassing an amino acid sequence, such as proteins, peptides, glycoproteins and lipoproteins;
- molecules generated by biological or synthetic means encompassing a nucleic acid sequence such as DNA and RNA fragments or oligonucleotides;
- other molecules resulting from a biological process or serving such a process such as cyclical adenosine monophosphate (AMP) or guanosine monophoshate (GMP);
- monosaccharides, polysaccharides and other macromolecules.

A multiwell plate is defined in connection with the present invention as an arrangement of open or closed chambers. This arrangement is preferably regular and constitutes a grid-like array of sample containers or sample holders. Known multiwell plates of this type are for instance the so-called microplates, with 96, 384 or 1536 wells arranged in a rectangular grid. The samples do not necessarily have to be arranged in depressions. Smaller samples can be also be arranged on a flat surface in an array and be separated from each other simply by hydrophobic sections or small elevations. Preferably, all multiwell plates have in common that a large number of samples with addressable positions can be processed simultaneously or essentially simultaneously.

Among others, known methods for measuring the fluorescence lifetime are the phase modulation technique and time correlated single photon counting (TCSPC). The present invention shall now be presented in more detail with reference to a selected exemplary experiment.

Experiment 1

In this experiment, the known method of time correlated single photon counting (TCSPC) for measuring the fluorescence lifetime was employed.

A) Technical Details:

The experiments were conducted with commercially available chemicals. In doing so, the following chemicals were used:

PTK Green as the tracer peptide, concentration 2 nM, P-2843 from PANVERA (PANVERA, 501 Charmany Drive, Madison Wis. USA), as part of the "green" kinase assay, in accordance with Kit No. P-2837;

PTP1B phosphatase, SE-332 from BIOMOL (BIOMOL Research Laboratories, Inc., 5120 Butler Pike, Plymouth Meeting Pa. USA 19462-1202);

fluorescein and PBS buffer.

The samples were prepared in black 384-well microplates from GREINER (GREINER Bio-One GmbH, Bad Haller Strasse 32, 4550 Kremsmünster, Austria) with a filled volume of 70 µl. The enzyme concentration was 100 pM to 100 nM. Incubation was undertaken for 30 minutes.

The fluorescence lifetime was measured using an "Ultra Evolution" machine with the fluorescence lifetime (FLT) option from TECAN (TECAN Austria GmbH, Grödig, Salzburg, Austria). The fluorescence laser operated at a wavelength of 440 nm and a repetition rate of 20 MHz. The emission filter was set to a wavelength of 544 nm and a bandwidth of 25 nm and the integration period per well was one second.

B) Results:

FIG. 1 shows the measured fluorescence lifetime of the fluorescent marker fluorescein, which is part of the tracer peptide (biomolecule), as a function of the enzyme concentration. Express reference is made here to the fact that no additional auxiliary molecule (such as an antibody or the like) had to be used to obtain these measurement results. Measurement was undertaken 30 minutes after the addition of the enzyme PTP1B to the tracer peptide. The fluorescence lifetime reflects the state of peptide phosphorylation, with higher enzyme concentrations working faster and producing more dephosphorylated peptide. The fluorescein bonded to the now dephosphorylated peptide exhibits a shorter lifetime.

After a very protracted period and regardless of the enzyme concentration, all phosphate groups would be removed from the tracer peptide. However, the enzyme concentration does determine the exact period required.

FIG. 1 also shows that when the enzyme concentration is very low, the state of phosphorylation is not altered significantly; on the other hand when the highest concentrations are used by adding still more enzymes, no additional effect can be demonstrated. In this experiment the entire substrate of the sample was converted during the incubation period, so that the proportion of the manifest enzyme function is apparent in the center. FIG. 1 is based on data for the dephosphorylation of Panvera tracer P2843 at various phosphatase concentrations. The error bars were produced from three independent measurements. The unbroken line is only to assist appreciation of dependency. The position of this line moves to the right when the incubation period is shorter and to the left when the period is longer. The z' value for the data set shown in FIG. 1 is 0.62.

Figure 2:
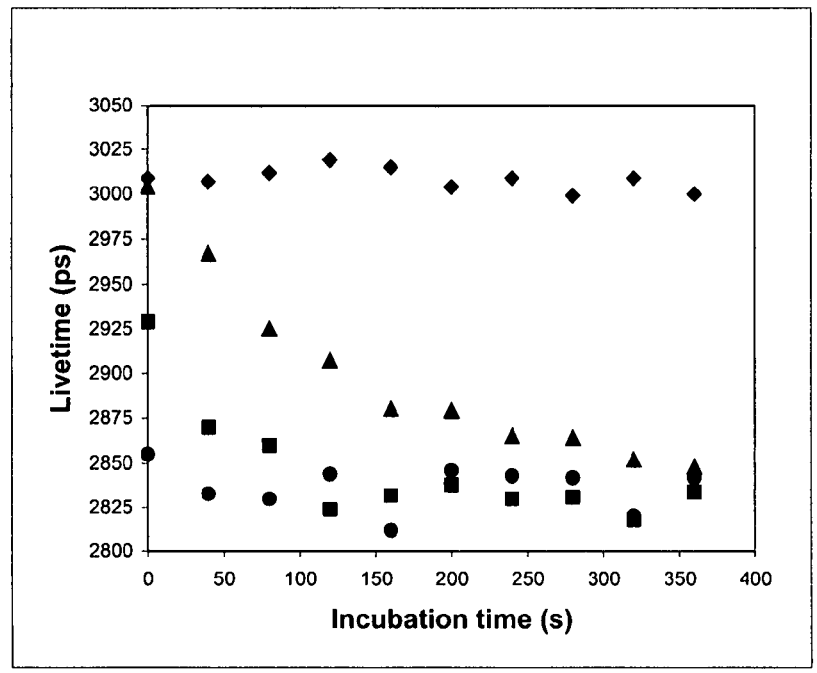

FIG. 2 shows the time-dependent nature of the enzyme reaction, i.e. the enzyme kinetics for various enzyme concentrations. Without enzymes the lifetime signal remains stable, i.e. no dephosphorylation occurs. When there is a moderate concentration one can see the entire process in the selected 6-minute period, and for very high concentrations the reaction occurs too quickly to be measurable in this experiment. The measurement points for the various enzyme concentrations are shown as diamonds (without enzymes), triangles (1 nM), squares (3 nM) or spots (30 nM).

In order to verify these results two samples with different fluorescence lifetime signals were measured using fluorescent polarization; no difference in the phosphorylation of the tracer peptide could be determined using this known method.

Experiments such as the one just described play an important role in assay development or in high throughput screening laboratories. Yet the apparatus previously available in such laboratories did not permit the measurement of fluorescence lifetimes.

As indicated at the outset, an enzyme reaction involving the phosphorylation or dephosphorylation of a peptide is of major biological and pharmacological significance. The present invention provides a novel method for analyzing and representing such important processes. In particular, preferred applications of the method in accordance with the invention include drug discovery screening, that is the discovery, research, optimization or validation and/or the detection of pharmacologically effective substances and/or in conjunction with the corresponding production of pharmaceutical preparations.

Within the scope of this present invention, attaching phosphate groups to a biomolecule must have a direct impact upon the fluorescent dye. For this to be the case, both groups have to be either in the vicinity of each other or the effect can be translated by means of the conformational transformation of biomolecules, which then modifies the molecular environment of the dye. Both chemical units, the phosphate group as well as the dye, have to be attached to the same biomolecule, for instance covalently. However, the biomolecule can also consist of several subunits, that is (hetero or homo) dimers, trimers, or in general oligomers. In this case the two residues can also be located on different subunits of the same biomolecule.

What is claimed is:

1. A method for measuring the phosphorylation state of biological molecules in a sample, consisting essentially of tagging said molecules with fluorescent markers and activating said fluorescent markers by irradiating the sample with light, the method further comprising the steps of:
   (a) selecting a fluorescent marker, whose fluorescence lifetime assumes a different value depending upon the presence or absence of phosphate groups in its vicinity;
   (b) attaching the fluorescent marker selected in step (a) to a biomolecule;
   (c) measuring the fluorescence lifetime of the fluorescent marker in a sample containing the biomolecule with the fluorescent marker attached in accordance with step (b); and
   (d) classifying the biomolecules in the sample in accordance with the presence or absence of phosphate groups attached to said biomolecules, while basing said classifying on the different lifetime of each fluorescence marker.

2. The method of claim 1, wherein the biological molecules comprise an amino acid sequence.

3. The method of claim 1 wherein the fluorescent marker is selected from the group which comprises fluorescein and fluorescein derivatives.

4. The method of claim 1, wherein the biological molecules of a sample are incubated with a phosphatase or with a phosphokinase prior to the measurement of the state of phosphorylation.

5. The method of claim 1 wherein one or more steps selected from the group of marking of biological molecules, activation of the assay, and measurement of the fluorescence lifetime is conducted in a multiwell plate with a computer for automatically classifying the biomolecules or the samples respectively.

6. The method of claim 1, wherein the measurement of the fluorescence lifetime is undertaken by means of time correlated single photon counting (TCSPC) or by means of the phase modulation technique.

7. The method of claim 1, wherein the proportion of the two species of biomolecules in the assay is quantified by means of calibration.

8. The method in accordance with claim 1 for drug discovery screening of chemical agents for pharmacologically effective substances.

9. The method in accordance with claim 1 for drug discovery screening of chemical agents for manufacturing pharmacological preparations.

10. The method in accordance with claim 1 for detecting defects in human or animal enzymes.

11. The method of claim 2, wherein the amino acid sequence selected from the group comprising: proteins, peptides, glycoproteins and lipoproteins.

12. The method of claim 1, wherein one or more steps selected from the group of marking of biological molecules, activation of the assay, and measurement of the fluorescence lifetime is conducted in a multiwell plate comprising a microplate with 96, 384 or 1536 wells and with a computer for automatically classifying the biomolecules or the samples respectively.

* * * * *